United States Patent [19]

Glaser et al.

[11] Patent Number: 4,870,085
[45] Date of Patent: Sep. 26, 1989

[54] TRYPTAMINE DERIVATIVES ACTIVE ON CENTRAL NERVOUS SYSTEM

[75] Inventors: Thomas Glaser; Siegfried Raddatz, both of Cologne; Jörg Traber, Lohmar, all of Fed. Rep. of Germany; Allen, George, Nashville, Tenn.

[73] Assignee: Bayer Aktiengesellschaft, Leverkusen, Fed. Rep. of Germany

[21] Appl. No.: 175,066

[22] Filed: Mar. 30, 1988

Related U.S. Application Data

[63] Continuation-in-part of Ser. No. 760,195, Jul. 29, 1985, abandoned.

[30] Foreign Application Priority Data

Aug. 17, 1984 [DE] Fed. Rep. of Germany ....... 3430284

[51] Int. Cl.$^4$ .................. A61K 31/40; A61K 31/445; C07D 209/16; C07D 211/14
[52] U.S. Cl. .................... 514/323; 514/414; 546/167; 546/201; 548/468
[58] Field of Search .............. 548/468; 546/201; 514/414, 323

[56] References Cited

U.S. PATENT DOCUMENTS

| | | | |
|---|---|---|---|
| 3,183,235 | 5/1965 | Zenitz | 546/201 |
| 3,642,803 | 2/1972 | Welstead, Jr. | 548/468 X |
| 3,732,248 | 5/1973 | Canas-Rodriguez et al. | 548/468 X |
| 3,907,812 | 9/1975 | Yamamato et al. | 546/201 X |
| 3,953,442 | 4/1976 | Demarne | 548/468 X |
| 4,435,410 | 3/1984 | LeFur et al. | 546/201 X |
| 4,478,841 | 10/1984 | Audiau et al. | 546/201 X |

OTHER PUBLICATIONS

C.A.; vol. 67, (1967); 89633n; Daleva, et al.,
C.A., vol. 94, (1981); 94:41139m; Guereny et al.
C.A., vol. 94, (1981); 94:47062c; Agarwal et al.,
C.A., vol. 91, (1979); 91:91438s; Fleming et al.
C.A., vol. 91, (1979); 91:168362x; Fukumori et al.

Primary Examiner—Joseph Paul Brust
Attorney, Agent, or Firm—Sprung Horn Kramer & Woods

[57] ABSTRACT

Novel tryptamines of the formula

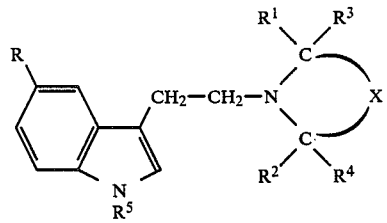

in which

X is an alkylene chain or 2 to 4 carbon atoms wherein a carbon atom may be replaced by O or N-lower alkyl, and wherein a carbon atoms may be substituted by lower alkyl, R is hydrogen, lower alkyl, lower alkoxy, phenyl-lower alkyl, phenyl-lower alkoxy, hydroxy, amino-lower alkyl, fluorine, chlorine, bromine, cyano, carbamoyl or azido, $R^1$, $R^2$, $R^3$ and $R^4$ each independently is hydrogen or lower alkyl, $R^5$ is hydrogen, $R^6$—CO— or $R^6$—SO$_2$—, and $R^6$ is amino, lower alkoxy, phenyl or lower alkyl-phenyl, or dimers or salts thereof, are effective in treating disorders of the central nervous system.

18 Claims, No Drawings

TRYPTAMINE DERIVATIVES ACTIVE ON CENTRAL NERVOUS SYSTEM

This is a continuation-in-part of application Ser. No. 760,195, filed July 29, 1985 now abandoned.

The invention relates to new tryptamines and their salts with physiologically acceptable acids, to a process for their preparation, and to their use for combating diseases.

The invention particularly relates to the use of these substances for the treatment of disorders of the central nervous system by an effect on the serotoninergic system.

The invention relates to tryptamines of the general formula I

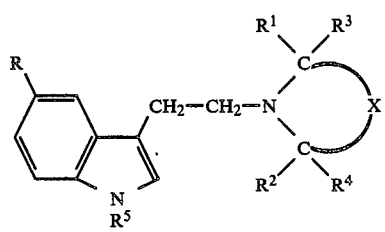

in which
- X is an alkylene chain of 2 to 4 carbon atoms wherein a carbon atom may be replaced by O or N-lower alkyl, and wherein a carbon atom may be substituted by lower alkyl,
- R is hydrogen, lower alkyl, lower alkoxy, phenyl-lower alkyl, phenyl-lower alkoxy, hydroxy, amino-lower alkyl, fluorine, chlorine, bromine, cyano, carbamoyl or azido,
- $R^1$, $R^2$, $R^3$ and $R^4$ each independently is hydrogen or lower alkyl,
- $R^5$ is hydrogen, $R^6$—CO— or $R^6$—SO$_2$—, and
- $R^6$ is amino, lower alkoxy, phenyl or lower alkyl-phenyl, in the cis form, in the trans form, and in the form of all mixtures of the two isomers of a dimer or salt thereof.

The compounds are prepared by the known process of M. E. Speeter and W. C. Anthonyl (J. Am. Chem. Soc. 76, 1954, 6208–10), by reacting indoles with oxalyl chloride, then with appropriate amine, and reducing the resulting oxamides with lithium aluminum hydride to give the tryptamines.

The reaction takes place according to the scheme below:

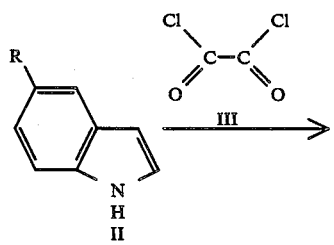

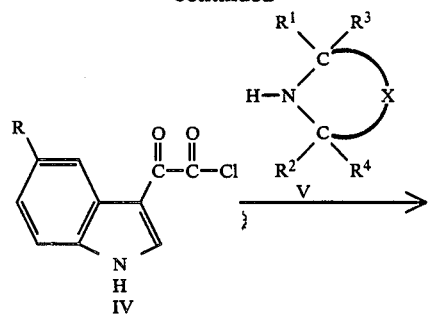

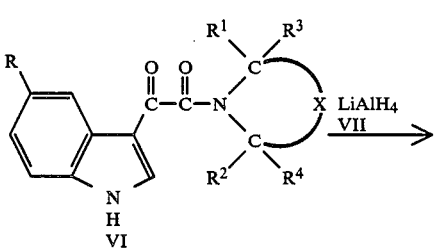

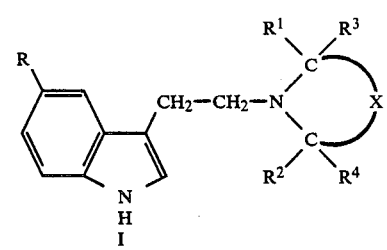

The 5-cyano compound can also be prepared by allowing the 5-bromo compound to react with copper(I) cyanide in boiling N-methyl-2-pyrrolidone (202° C.) in analogy to M. S. Newman, J. Org. Chem. 26, 1961, 1961, 2525 (compare Example 6).

The 5-carbamoyl compound is prepared by heating the 5-cyano compound with potassium hydroxide in tert.-butanol under reflux for about seven hours by the method of J. Hall, J. Org. Chem. 41, 1976, 3769.

A dimer is prepared from two molecules wherein $R^5$ is hydrogen and R is a replaceable radical which reacts with the $R^5$ hydrogen of another molecule, e.g. Br or CN, splitting out HBr, HCN, or the like.

The active compounds of the formula I, according to the invention, differ from known tryptamines by the basic nitrogen being located in a ring and being highly sterically shielded by substituents in the immediate neighborhood. These compounds have a special conformation which has been unambiguously established and which permits the occupation of, for example, very particular subtypes of serotonin receptors in the brain, in particular those of the 5-HT$_1$ type (see Table).

5-HT$_1$ receptors have been detected in particular parts of the human brain (J. M. Palacios et al., Brain Research 274, 1983, 150–155) and in blood vessels of the central nervous system (S. J. Peroutka and M. J. Kuhar, Brain Research, 310, 1984, 193–196).

The compounds according to the invention interact selectively with these 5-HT$_1$ receptors in the brain. In suitable designs of experiments, they have antagonistic effects, for example the contraction of the basilar artery of the dog induced by serotonin (5-hydroxytryptamine=5-HT) via 5-HT$_1$ receptors (S. J. Peroutka et al., Brain Research 259, 1983, 327-330) is blocked by the active compounds according to the invention.

Moreover, the increase in the adenylate cyclase activity of neural NCB-20 cells brought about by serotonin (Lit.: E. Berry-Kravis and G. Dawson, J. Neurochem. 41, 1983, 977-985) is presented by the compounds according to the invention.

Thus the compounds are selective 5-HT$_1$ antagonists. Because of these properties, the compounds according to the invention are suitable for the treatment of disorders of the central nervous system, in particular for the treatment of sleep disturbances, migraine, vasospasms and ischaemias. Hence they represent an enrichment of the drug armamentarium.

Preferred compounds of the formula I are those in which

X is an alkylene chain of 2 to 4 carbon atoms which can be substituted by lower alkyl, R represents hydrogen, fluorine, chlorine, bromine, methyl, methoxy, benzyloxy, hydroxy, cyano or aminomethyl, $R^1$, $R^2$, $R^3$ and $R^4$ each independently is hydrogen or lower alkyl, $R^5$ is hydrogen, $R^6$—CO— or $R^6$—SO$_2$—, and $R^6$ is amino, t-butoxy, phenyl or tolyl.

Particularly preferred compounds of the formula I are those in which

X is an alkylene of 3 carbon atoms,

R is hydrogen, bromine, chlorine or aminocarbonyl, $R^1$ and $R^2$ are methyl, $R^3$ and $R^4$ are hydrogen, and $R^5$ is hydrogen.

The preparation of the compounds is indicated by the reaction scheme on page 2. The starting materials of the formulae II, III and VII are commercially available, and the compounds V are either commercially available or can be prepared by known methods (for example H. . House and L. F. Lee, J. Org. Chem. 41, 1976, 863–9).

The 5-cyano compound can also be prepared from the 5-bromo compound by boiling under reflux with copper(I) cyanide in N-methyl-2-pyrrolidone.

The 5-carbamoyl compound is obtained by reaction of the 5-cyano compound with potassium hydroxide in boiling tert.-butanol.

The present invention includes pharmaceutical preparations which in addition to non-toxic, inert pharmaceutically suitable excipients contain one or more compounds according to the invention or their salts or which consist of one or more compounds according to the invention or their salts, and processes for the production of these preparations.

The present invention also includes pharmaceutical preparations in dosage units. This means that the preparations are in the form of individual parts, for example tablets, coated tablets, capsules, pills, suppositories and ampules, of which the content of active compound corresponds to a fraction or a multiple of an individual dose. The dosage units can contain, for example 1, 2, 3 or 4 individual doses or ½, ⅓ or ¼ of an inidividual dose. An individual dose preferably contains the amount of active compound which is given in one administration and which usually corresponds to a whole, a half or a third or a quarter of a daily dose.

By non-toxic, inert pharmaceutically suitable excipients there are to be understood solid, semi-solid or liquid diluents, fillers and formulation auxiliaries of all kinds.

Tablets, coated tablets, capsules, pills, granules, suppositories, solutions, suspensions and emulsions may be mentioned as preferred pharmaceutical preparations.

Tablets, coated tablets, capsules, pills and granules can contain the active compound or compounds alongside the customary excipients such as (a) fillers and extenders, for example starch, lactose, sucrose, glucose, mannitol and silica, (b) binders, for example carboxymethylcellulose, alginates, gelatine and polyvinylpyrrolidone, (c) humectants, for example glycerol, (d) disintegrants, for example agar-agar, calcium carbonate and sodium bicarbonate, (e) solution retarders, for example paraffin, (f) absorption accelerators, for example quaternary ammonium compounds, (g) wetting agents, for example cetyl alcohol and glycerol monostearate, (h) adsorbents, for example kaolin and bentonite, and (i) lubricants, for example talc, calcium and magnesium stearate and solid polyethylene glycols, or mixtures of the substances listed under (a) to (i).

The tablets, coated tablets, capsules, pills and granules can be provided with the customary coatings and shells, optionally containing opacifying agents, and can also be of such composition that they release the active compound or compounds only, or preferentially, in a certain part of the intestinal tract, optionally in a delayed manner, examples of embedding compositions which can be used being polymeric substances and waxes.

The active compound or compounds, optionally together with one or more of the abovementioned excipients, can also be in a microencapsulated form.

Suppositories can contain, in addition to the active compound or compounds, the customary water-soluble or water-insoluble excipients, for example polyethylene glycols, fats, for example cacao fat, and higher esters (for example $C_{14}$-alcohol with $C_{16}$-fatty acid) or mixtures of these substances.

Solutions and emulsions can contain the customary excipients in addition to the active compound or compounds, such as solvents, solubilizing agents and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, especially cottonseed oil, groundnut oil, corn germ oil, olive oil, castor oil and sesame oil, glycerol, glycerol-formal, tetrahydrofurfuryl alcohol, polyethylene glycols and fatty acid esters of sorbitan, or mixtures of these substances.

For parenteral administration, the solutions and emulsions can also be in a sterile form which is isotonic with blood.

Suspensions can contain the customary excipients in addition to the active compound or compounds, such as liquid diluents, for example water, ethyl alcohol or propylene glycol, suspending agents, for example ethoxylated isostearyl alcohls, polyoxyethylene sorbitol esters and sorbitan esters, microcrystalline cellulose, aluminum metahydroxide, bentonite, agar-agar and tragacanth, or mixtures of these substances.

The formulation forms mentioned can also contain dyestuffs, preservatives and additives which improve the odor and flavor, for example peppermint oil and eucalyptus oil, and sweeteners, for example saccharin.

The therapeutically active compounds should preferably be present in the abovementioned pharmaceutical preparations in a concentration of about 0.1 to 99.5, preferably of about 0.5 to 95, % by weight of the total mixture. The abovementioned pharmaceutical formulations can also contain other pharmaceutical active compounds in addition to compounds of the formula I and/or their salts.

The abovementioned pharmaceutical preparations are manufactured in the usual manner according to known methods, for example by mixing the active compound or compounds with the excipient or excipients.

The present invention also includes the use of the compounds of the formula I and/or of their salts and of pharmaceutical preparations which contain one or more compounds of the formula I and/or their salts in human medicine for the prevention, amelioration and/or cure of the abovementioned disorders.

The active compounds or the pharmaceutical preparations can be administered preferably orally, parenterally and/or rectally, preferably orally and parenterally, especially orally and intravenously.

In general, it has proved advantageous in the case of parenteral (i.v. or i.m.) administration to administer the active compound or compounds in amounts of about 0.005 to about 5, preferably 0.01 to 1, mg/kg of body weight every 24 hours, and in the case of oral administration in amounts of about 0.01 to about 10, preferably 0.05 to 5, mg/kg of body weight every 24 hours, optionally in the form of several individual administrations, in order to achieve the desired results. An individual administration contains the active compound or compounds preferably in amounts of about 0.005 to about 10, in particular 0.01 to 1, mg/kg of body weight.

However, it can be necessary to deviate from the dosages mentioned and in particular to do so as a function of the nature and body weight of the subject to be treated, the nature and severity of the disorder, the nature of the preparation and of the administration of the medicine, and the time or interval over which the administration takes place. Thus, it can suffice in some cases to manage with less than the abovementioned amount of active compound, while in other cases the abovementioned amount of active compound must be exceeded. The particular required optimum dosage and the type of administration of the active compounds can easily be decided by anyone skilled in the art on the basis of his expert knowledge.

The present invention also includes medicines which in addition to compounds of the formula I contain other active compounds. The following may be mentioned as being preferred: β-receptor blockers, parasympatholytics, anxiolytics, neuroleptics, hypnotics and tranquillizers.

EXAMPLE 1

3-[2-(Cis- and trans-2,5-dimethylpyrrolidinyl)ethyl]indole hydrochloride

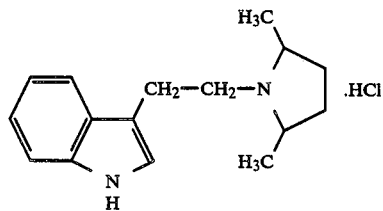

1.1

Indolyl-3-glyoxyl chloride 10 g (0.085 mol) of oxalyl chloride are dissolved in diethyl ether and, while stirring, 11.1 g (0.088 mol) of indole in 25 ml of diethyl ether are added dropwise. The addition is metered such that the ether just boils and the evolution of hydrogen chloride is not too vigorous. To complete the reaction, the mixture is boiled for a further two hours. On cooling, colorless (sometimes pale green-colored) crystals separate out; melting point: 138° C.

Yield: 15.7 g (89% of theory)

1.2

Indolyl-3-glyoxyl cis- and trans-2,5-dimethylpyrrolidide 10 g (0.048 mol) of indolyl-3-glyoxyl chloride are dissolved in 200 ml of tetrahydrofuran (THF) and, while stirring, a mixture of 4.9 g 0.049 mol)=6.1 ml of 2,5-dimethylpyrrolidine (cis/trans mixture) and 4.9 g of triethylamine (0.049 mol)=6.7 ml in 100 ml of THF is added dropwise. Reaction takes place immediately. After allowing to react for a further hour, the mixture is evaporated to dryness in vacuo, and the residue is taken up in 100 ml of dichloromethane, the solution is extracted by shaking twice with 50 ml of water, and the organic phase is dried with sodium sulphate, evaporated to a small volume and the residue is chromatographed (silica gel 60, mobile phase: dichloromethane/ethyl acetate=4/1. Colorless crystals with a melting point of 140° C. are obtained.

Yield: 10.3 g (80% of theory).

1.3

Cis- and trans-3-[2-(2,5-dimethylpyrrolidinyl)ethyl]-indole hydrochloride 5.6 g (0.148 mol) of lithium aluminum hydride are suspended in 400 ml of THF and, while stirring at room temperature, 10 g (0.37 mol) of indolyl-3-glyoxyl cis- and trans-2,5-dimethylpyrrolidide are added dropwise. The evolution of gas starts gradually. The reaction is completed by then boiling for five hours.

After cooling, cautious addition, while cooling, of 5.6 ml of water, 4 ml of 20% strength sodium hydroxide solution and then 18 ml of water is carried out. The resulting precipitate is filtered off, extracted by stirring with about 50 ml of THF and again filtered. The combined filtrates are evaporated to dryness and the residue is dissolved in 100 ml of methanol. About 50 ml of 50% strength hydrochloric acid are added, and the mixture is evaporated to dryness in vacuo, and the residue is taken up in 50 ml of water. After addition of 20 ml of 5N sodium hydroxide solution (to make alkaline), the mixture is extracted by shaking three times with 50 ml of dichloromethane. The organic phases are combined, dried with sodium sulphate and, after evaporation to a small volume, chromatographed (alumina 90, activity 2-3, mobile phase: dichloromethane/ethyl acetate=4/1). Two fractions are obtained. The solutions are evaporated to dryness and the residues are recrystallized from cyclohexane. Colorless crystals are obtained in each case.

Cis-product: Melting point:=139° C., yield 4.8 g (53% of theory) trans-product: melting point:=154° C., yield 3.0 g (34% of theory). The conformations are assigned with the aid of $^{13}$C-NMR spectroscopy.

Hydrochlorides

The particular amine is dissolved in dichloromethane/isopropanol, and 1N hydrochloric acid is added. After evaporation to dryness, the product is recrystallized from isopropanol/diisopropyl ether=1/1, and colorless crystals are obtained in each case.

Cis-product: melting point=220° C. (decomposition), yield 93% of theory trans-product: melting point=205° C. (decomposition), yield: 84% of theory.

EXAMPLE 2

3-[2-(Cis-2,6-dimethylpiperidinyl)ethyl]indole hydrochloride

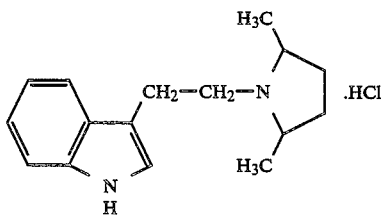

2.1

Indolyl-3-glyoxyl chloride

In analogy to 1.1. from 111.7 g (0.88 mol)=75 ml of oxalyl chloride and 100 g (0.853 mol) of indole colorless crystals; melting point: 138°-9° C. Yield: 158.8 g (90% of theory).

2.2

Indolyl-3-glyoxyl cis-2,6-dimethylpiperidide

In analogy to 1.2. from 10.4 g (0.05 mol) of indolyl-3-glyoxyl chloride and 10.1 g (0.1 mol)=12.0 ml of 2,6-cis-dimethylpiperidine colorless crystals; melting point: 196° C.

Yield: 12.5 g (46% of theory).

2.3

3-[2-(Cis-2,6-dimethylpiperidinyl)ethyl]indole hydrochloride

In analogy to 1.3. from 3.0 g (0.079 mol) of lithium aluminum hydride and 5.5 g (0.02 mol) of indolyl-3-glyoxyl cis-2,6-dimethylpiperidide, chromatography with silica gel 60, mobile phase: methanol/dichloromethane=15/85; recrystallization from diisopropyl ether colorless crystals; melting point: 168° C. hydrochloride.

colorless crystals; melting point: 280°-2° C. (decomposition).

Yield: 4.7 g (81% of theory).

EXAMPLE 3

3-[2-(Cis-2,6-dimethylpiperidinyl)ethyl]-5-bromoindole hydrochloride

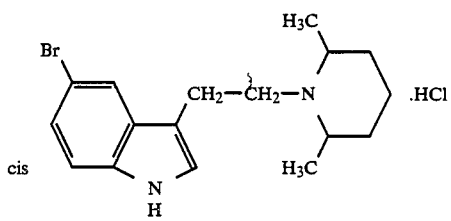

3.1

5-Bromoindolyl-3-glyoxyl cis-2,6-dimethylpiperidide 6.4 g (0.05 mol)=4.4 ml of oxalyl chloride are dissolved in 100 ml of THF in a 500 ml three-necked flask (CaCl$_2$ tube, reflux condenser, nitrogen introduction tube) and, at 50° C., 9.8 g (0.05 mol) of 5-bromoindole in 50 ml of THF are added dropwise. A TLC check shows that the reaction is complete after about one hour. The mixture is allowed to cool to room temperature and, while stirring, 17.1 g (0.15 mol)=20.4 ml of cis-2,6-dimethylpiperidine in 50 ml of THF are added dropwise. While warming slightly the solution changes color to pale yellow, and a colorless precipitate separates out. The mixture is then stirred for one hour until a TLC check shows that intermediate is no longer present. After evaporation to dryness, the residue is extracted by stirring with 100 ml of water. A yellow oil floats on the water, and this is extracted three times with 50 ml of dichloromethane. After drying with sodium sulphate, the solution is evaporated to a small volume and chromatographed (silica gel 60, mobile phase: dichloromethane/methanol=20/1). The main fraction obtained is evporated to dryness, and the residue is recrystallized from ethyl acetate.

Colorless crystals; melting point: 227° C.

Yield: 5.8 g (32% of theory based on 5-bromoindole).

3.2

3-[2-(Cis-2,6-dimethylpiperidinyl)ethyl]-5-bromoindole hydrochloride

In analogy to 1.3. from 2.0 g (0.055 mol) of lithium aluminum hydride and 5.0 g (0.0138 mol) of 5-bromoindolyl-3-glyoxyl cis-2,6-dimethylpiperidide. Chromatography (silica gel 60, dichloromethane/methanol=1/1), recrystallization from diisopropyl ether colorless crystals; melting point: 172° C.

Yield: 2.3 g (50% of theory) hydrochloride colorless crystals; melting point:=239° C. (decomposition), yield: 90% of theory.

EXAMPLE 4

3-[2-(Cis-2,6-dimethylpiperidinyl)ethyl]-5-chloroindole hydrochloride

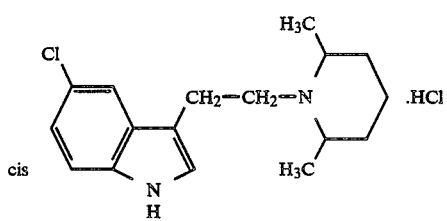

4.1

5-Chloroindolyl-3-glyoxyl cis-2,6-dimethylpiperidide

In analogy to 3.1. from 6.4 g (0.05 mol)=4.4 ml of oxalyl chloride, 7.6 g (0.05 mol) of 5-chloroindole and 17.1 g (0.15 mol)=20.4 ml of cis-2,6-dimethylpiperidine recrystallization from dichloromethane
 colorless crystals; melting point: 235° C.
 Yield: 4.3 g (27% of theory, based on 5-chloroindole).

4.2

3-[2-(Cis-2,6-dimethylpiperidinyl)ethyl]-5-chloroindole hydrochloride

In analogy to 1.3. from 1.1 g (0.031 mol) of lithium aluminum hydrochloride and 2.5 g (0.0078 mol) of 5-chloroindolyl-3-glyoxyl cis-2,6-dimethylpiperidide
 colorless crystals; melting point: 167° C.
 Yield: 1.7 g (74% of theory). hydrochloride
 colorless crystals; melting point 240°-3° C. (decomposition).
 Yield; 1.7 g (89% of theory).

EXAMPLE 5

3-[2-Cis-[2,6-dimethylpiperidinyl)ethyl]-5-fluoroindole hydrochloride

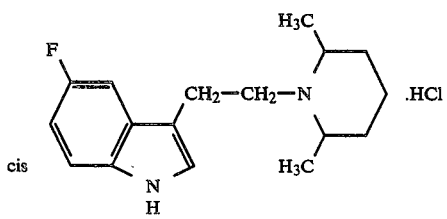

5.1

5-Fluoroindolyl-3-glyoxyl cis-2,6-dimethylpiperidide

In analogy to 3.1. from 4.7 g (0.037 mol)=3.3 ml of oxalyl chloride, 5.0 g (0.037 mol) of 5-fluoroindole and 12.6 g (0.111 mol)=15 ml of cis-2,6-dimethylpiperidine recrystallization from dichloromethane
 colorless crystals; melting point: 230° C.
 Yield: 4.9 g (44% of theory based on 5-fluoroindole).

5.2

3-[2-(Cis-2,6-dimethylpiperidinyl)ethyl]-5-fluoroindole hydrochloride

In analogy to 1.3. from 2.0 g (0.053 mol) of lithium aluminum hydride and 4.0 g (0.013 mol) of 5-fluoroindolyl-3-glyoxyl cis-2,6-dimethylpiperidide
 colorless crystals; melting point: 182° C.
 Yield; 2.5 g (69% of theory) hydrochloride
 colorless crystals; melting point: 295° C. (decomposition)
 Yield: 2.1 g (93% of theory).

The action of the compounds according to the invention is described below by the interaction with serotonin receptors.

EXAMPLE 6

3-[2-(Cis-2,6-dimethylpiperidinyl)ethyl]-5-cyanoindole hydrochloride

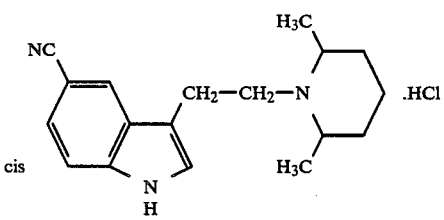

1.7 g (0.005 mol) of 3-[2-(cis-2,6-dimethylpiperidinyl)ethyl]-5-bromoindole (compare Example 3) and 0.82 g (0.0092 mol) of copper(I) cyanide are suspended in 10 ml of N-methyl-2-pyrrolidone and boiled under nitrogen four hours (oil bath: 205;20 -210° C. ). Starting compound is no longer present according to a TLC check (mobile phase: methanol/DMF=1/1). The mixture is diluted with 30 ml of methanol, the insolubles are filtered off, and 100 ml of water are added to the filtrate. The precipitated product is filtered, dried and chromatographed (silica gel 60, mobile phase: methanol/DMF=1/1). The suitable fractions are evaporated to dryness and the residue is recrystallized from diethyl ether.
 colorless crystals; melting point: 140° C.
 Yield: 0.1 g (7% of theory). hydrochloride.
 colorless crystals; melting point: 220° C. (decomposition).

EXAMPLE 7

TABLE 1

| | Interaction with serotonin receptors | | | |
|---|---|---|---|---|
| | Inhibition constant $K_i$ (nmol $l^{-1}$) | | Antagonism | |
| Test substance | 5-HT$_1$ receptor calf hippocampus Ligand: $^3$H—serotonin | 5-HT$_2$ receptor rat prefrontal cortex Ligand: $^3$H—ketanserin | NCB-20 cells Adenylate cyclase | Contraction of the basilar artery - dog |
| Example 2 | 150 | 2,500 | + | + |
| Example 3 | 50 | 1,300 | + | + |

References
P. Seemann et al., Eur. J. Pharmacol 66 (1980), 179-191
J. E. Leysen et al., Mol. Pharmacol. 21 (1982), 301-314
E. Berry-Kravis and G. Dawson, J Neurochem. 41 (1983), 977-985
S. J. Peroutka et al., Brain Res. 259 (1983), 327-330

EXAMPLE 8

3-[2-(Cis-2,6-dimethylpiperidinyl)ethyl]-5-methylindole hydrochloride

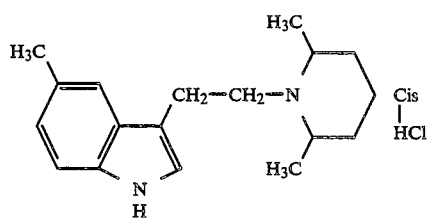

8.1

5-Methylindolyl-3-glyoxyl cis-2,6-dimethylpiperidide

Analogously to Example 3.1 4,9 g=3,4 ml (0,038 mol) of oxalylchloride are reacted with 5,0 g (0,0381 mol) of 3-methylindole and 13,0 g=15,5 ml (0,115 mol) of cis-2,6-Dimethylpiperidine.

Recrystallization from ethyl acetate/Isopropylether (1:1) colorless crystals; melting point: 220° C. (decomposition)

Yield: 7,9 g (70% of theory).

8.2

3-[2-Cis-2,6-dimethylpiperidinyl)ethyl]-5-bromoindole hydrochloride

Analogously to Example 1.3. from 3,6 g (0,094 mol) of lithiumaluminumhydride are reacted with 7,0 g (0,0234 mol) of cis-5-methyl-3-glyoxyl-2,6-dimethylpiperidide from Example 8.1.

Colorless crystals, melting point: 148° C.

Yield: 2,5 g (40% of theory).

Hydrochloride.

Colorless crystals, melting point: 276° C. (decomposition).

Yield: 2,7 g (97% of theory).

EXAMPLE 9

In generally similar manner there were prepared additional compounds which, when tested against 5-HT, receptors as in Example 7, gave the results shown in Table 2.

TABLE 2

| Compound No. | Structure | $K_1$ (n mol $1^{-1}$) 5-HT$_1$ receptor calf hippocampus Ligand 3H—serotonin |
|---|---|---|
| 8 | ![structure] | |
| 9 | ![structure] | 13 |
| 10 | ![structure] | 10 |
| 11 | ![structure] | 200 |

TABLE 2-continued

| Compound No. | Structure | $K_i$ (n mol $1^{-1}$) 5-HT$_1$ receptor calf hippocampus Ligand 3H—serotonin |
|---|---|---|
| 12 | 5-hydroxy-3-[2-(cis-2,6-dimethylpiperidin-1-yl)ethyl]-1H-indole · HCl | 15 |
| 13 | 3-[2-(cis-2,6-dimethylpiperidin-1-yl)ethyl]-1-carbamoyl-1H-indole · HCl | 1800 |
| 14 | 5-benzyloxy-3-[2-(cis-2,6-dimethylpiperidin-1-yl)ethyl]-1H-indole · HCl | 800 |
| 15 | 5-benzyloxy-3-[2-(trans-2,6-dimethylpiperidin-1-yl)ethyl]-1H-indole · HCl | 500 |
| 16 | 5-hydroxy-3-[2-(cis-2,6-dimethylpiperidin-1-yl)ethyl]-1H-indole · HCl | 4 |
| 17 | 5-hydroxy-3-[2-(trans-2,6-dimethylpiperidin-1-yl)ethyl]-1H-indole · HCl | 25 |

TABLE 2-continued

| Compound No. | Structure | $K_1$ (n mol $1^{-1}$) 5-HT$_1$ receptor calf hippocampus Ligand 3H—serotonin |
|---|---|---|
| 18 | 5-Br-indole-CH$_2$CH$_2$-N(cis-2,6-dimethylpiperidine)·HCl | 30 |
| 19 | indole-CH$_2$CH$_2$-N(cis-2,6-dimethylpiperidine)·HCl | 800 |
| 20 | 5-H$_3$CO-indole-CH$_2$CH$_2$-N(trans-2,6-dimethylpiperidine)·HCl | 450 |
| 21 | 5-H$_3$CO-indole-CH$_2$CH$_2$-N(cis-2,6-dimethylpiperidine)·HCl | 70 |
| 22 | 5-H$_3$CO-indole-CH$_2$CH$_2$-N(trans-2,6-dimethylpiperidine)·HCl | 45 |
| 23 | 5-Cl-indole-CH$_2$CH$_2$-N(cis-2,6-dimethylpiperidine)·HCl | 60 |
| 24 | 5-F-indole-CH$_2$CH$_2$-N(cis-2,6-dimethylpiperidine)·HCl | 170 |

TABLE 2-continued

| Compound No. | Structure | $K_i$ (n mol $l^{-1}$) 5-HT$_1$ receptor calf hippocampus Ligand 3H—serotonin |
|---|---|---|
| 25 | 3-(2-(2-methylpiperidin-1-yl)ethyl)-1H-indole · HCl | 170 |
| 26 | 3-(2-(2,4,6-trimethylpiperidin-1-yl)ethyl)-1H-indole · HCl | 920 |
| 27 | 5-methyl-3-(2-(cis-2,6-dimethylpiperidin-1-yl)ethyl)-1H-indole · HCl | 40 |
| 28 | 5-cyano-3-(2-(cis-2,6-dimethylpiperidin-1-yl)ethyl)-1H-indole · HCl | 240 |
| 29 | 3-(2-(trans-2,6-dimethylpiperidin-1-yl)ethyl)-1H-indole · HCl | 3000 |
| 30 | 1-(tert-butoxycarbonyl)-3-(2-(cis-2,6-dimethylpiperidin-1-yl)ethyl)-1H-indole · HCl | 1800 |

TABLE 2-continued
| Compound No. | Structure | $K_1$ (n mol $1^{-1}$) 5-HT$_1$ receptor calf hippocampus Ligand 3H—serotonin |
|---|---|---|
| 31 | 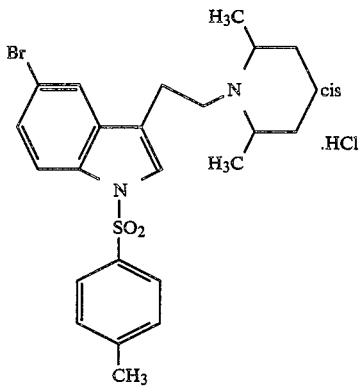 | 3200 |
| 32 | 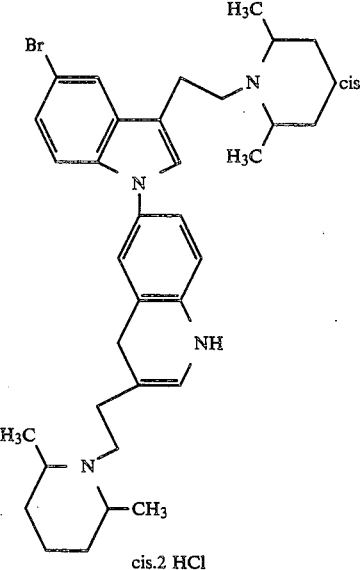 cis.2 HCl | 680 |
| 33 | 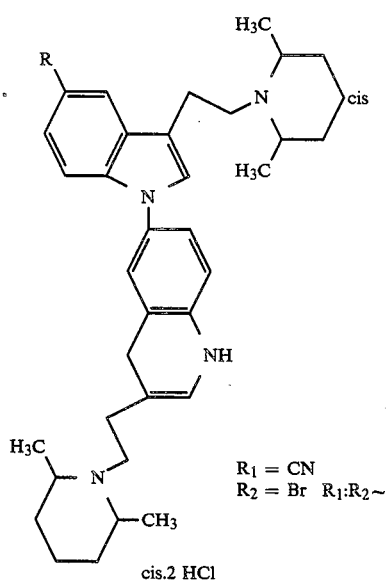 $R_1 = CN$ $R_2 = Br$ $R_1:R_2 \sim 4:1$ cis.2 HCl | 270 |

TABLE 2-continued

| Compound No. | Structure | $K_1$ (n mol $l^{-1}$) 5-HT$_1$ receptor calf hippocampus Ligand 3H—serotonin |
|---|---|---|
| 34 | 5-Br, N-methyl indole with ethyl-(cis-2,6-dimethylpiperidine) side chain · HCl | 1100 |
| 35 | 5-(H$_2$N—CH$_2$) indole with ethyl-(cis-2,6-dimethylpiperidine) side chain · 2 HCl | 500 |
| 36 | 5-Br, N-benzoyl indole with ethyl-(cis-2,6-dimethylpiperidine) side chain · HCl | 1000 |
| 37 | 5-(H$_2$N—CO) indole with ethyl-(cis-2,6-dimethylpiperidine) side chain · HCl | 7 |
| 38 | 5-Cl indole with ethyl-(2,4,6-trimethylpiperidine) side chain · HCl | 660 |
| 39 | Indole with ethyl-(2,2,6,6-tetramethylpiperidine) side chain · HCl | >10000 |

It will be understood that the specification and examples are illustrative but not limitative of the present invention and that other embodiments within the spirit

We claim:
1. A tryptamine of the formula

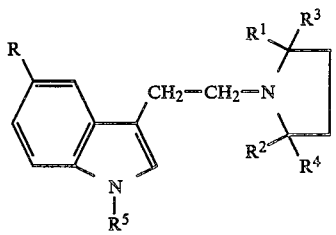

in which
R is hydrogen, lower alkyl, lower alkoxy, phenyl-lower alkyl, phenyl-lower alkoxy, hydroxy, amino-lower alkyl, fluorone, chlorine, bromine, cyano, carbamoyl or azido,
$R^1$ and $R^2$ each independently is lower alkyl,
$R^3$ and $R^4$ each independently is hydrogen or lower alkyl,
$R^5$ is hydrogen, $R^6$—CO— or $R^6$—SO$_2$— and
$R^6$ is amino, lower alkoxy, phenyl or lower alkyl-phenyl,
or a pharmaceutically acceptable salt thereof.

2. A tryptamine or pharmaceutically acceptable salt thereof according to claim 1, in which
R is hydrogen, fluorine, chlorine, bromine, methyl, methoxy, benzyloxy, hydroxy, cyano or amino-methyl,
$R^1$ and $R^2$ each is methyl,
$R^3$ and $R^4$ each independently is hydrogen or methyl, and
$R^6$ is amino, t-butoxy, phenyl or tolyl.

3. A tryptamine according to claim 1, wherein said tryptamine is 3-[2-(2,5-dimethylpyrrolidinyl)ethyl] indole of the formula

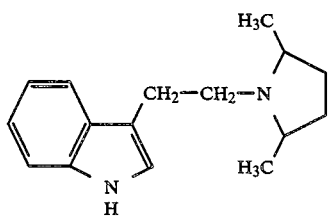

or a pharmaceutically acceptable salt thereof.

4. A composition for treatment of disorders of the central nervous system comprising an amount effective therefor of a tryptamine or pharmaceutically acceptable salt thereof according to claim 1 in admixture with a diluent.

5. A unit dose of a composition according to claim 1 in the form of a tablet, capsule or ampule.

6. A method of treating a disorder of the central nervous system which comprises administering to a patient suffering therefrom an amount effective therefor of a tryptamine or pharmaceutically acceptable salt according to claim 1.

7. A method of treating a disorder of the central nervous system which comprises administering to a patient suffering therefrom an amount effective therefor of a tryptamine or pharmaceutically acceptable salt according to claim 3.

8. A tryptamine of the formula

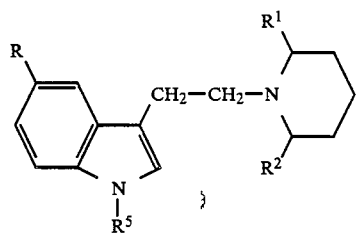

in which
R is hydrogen, lower alkyl, lower alkoxy, phenyl-lower alkyl, phenyl-lower alkoxy, hydroxy, amino-lower alkyl, fluorine, chlorine, bromine, cyano, carbamoyl or azido,
$R^1$ and $R^2$ each independently is lower alkyl,
$R^5$ is hydrogen, $R^6$—CO— or $R^6$—SO$_2$— and
$R^6$ is amino, lower alkoxy, phenyl or lower alkyl-phenyl,
or a pharmaceutically acceptable salt thereof.

9. A tryptamine or pharmaceutically acceptable salt thereof according to claim 8, in which
R is hydrogen, bromine, chlorine or carbamoyl,
$R^1$ and $R^2$ are methyl, and
$R^5$ is hydrogen.

10. A tryptamine according to claim 8, wherein said tryptamine is 3-[2-(2,6-dimethylpiperidinyl)ethyl]indole of the formula

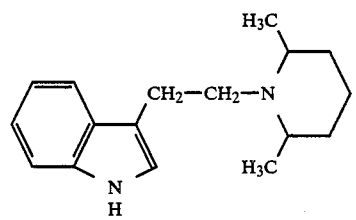

or a pharmaceutically acceptable salt thereof.

11. A tryptamine according to claim 8, wherein said tryptamine is 3-[2-(2,6-dimethylpiperidinyl)ethyl]-5-bromoindole of the formula

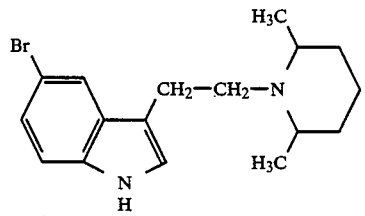

or a pharmaceutically acceptable salt thereof.

12. A tryptamine according to claim 8, wherein said tryptamine is 3-[2-(2,6-dimethylpiperidinyl)ethyl]-5-chloroindole of the formula

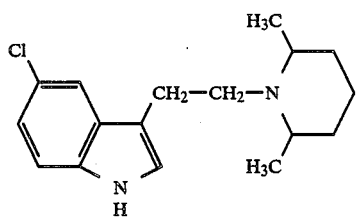

or a pharmaceutically acceptable salt thereof.

13. A tryptamine according to claim 8, wherein said tryptamine is 3-[2-(2,6-dimethylpiperidinyl)ethyl]-5-fluoroindole of the formula

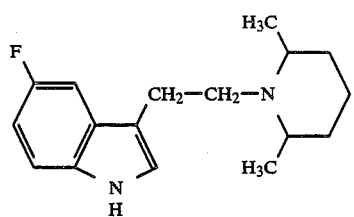

or a pharmaceutically acceptable salt thereof.

14. A tryptamine according to claim 8, wherein said tryptamine is 3-[2-(2,6-dimethylpiperidinyl)ethyl]-5-carbamoylindole of the formula

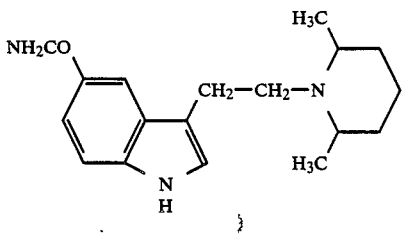

or a pharmaceutically acceptable salt thereof.

15. A composition for treatment of disorders of the central nervous system comprising an amount effective therefor of a tryptamine or pharmaceutically acceptable salt thereof according to claim 8 in admixture with a diluent.

16. A unit dose of a composition according to claim 15 in the form of a tablet, capsule or ampule.

17. A method of treating a disorder of the central nervous system which comprises administering to a patient suffering therefrom an amount effective therefor of a tryptamine or pharmaceutically acceptable salt thereof according to claim 8.

18. The method according to claim 17, wherein said tryptamine is
3-[2-(2,6-dimethylpiperidinyl)ethyl]indole,
3-[2-(2,6-dimethylpiperidinyl)ethyl]-5-chloroindole,
3-[2-(2,6-dimethylpiperidinyl)ethyl]-5-fluoroindole, or
3-[2-(2,6-dimethylpiperidinyl)ethyl]-5-carbamoylindole
or a pharmaceutically acceptable salt thereof.

* * * * *

UNITED STATES PATENT AND TRADEMARK OFFICE
CERTIFICATE OF CORRECTION

PATENT NO. : 4,870,085

Page 1 of 2

DATED : September 26, 1989

INVENTOR(S) : Glaser et al.

It is certified that error appears in the above-identified patent and that said Letters Patent is hereby corrected as shown below:

| | |
|---|---|
| Col. 23, line 18 | Delete " fluorone " and substitute -- fluorine -- |
| Col. 23, line 26 | Delete " pharmaceutically " and substitute -- pharmacologically -- |
| Col. 23, line 27 | Delete " pharmaceutically " and substitute -- pharmacologically -- |
| Col. 23, line 49 | Delete " pharmaceutically " and substitute -- pharmacologically -- |
| Col. 23, line 53 | Delete " pharmaceutically " and substitute -- pharmacologically -- |
| Col. 23, line 61 | Delete " pharmaceutically " and substitute -- pharmacologically -- |
| Col. 23, line 66 | Delete " pharmaceutically " and substitute -- pharmacologically -- |
| Col. 24, line 25 | Delete " pharmaceutically " and substitute -- pharmacologically -- |
| Col. 24, line 26 | Delete " pharmaceutically " and substitute -- pharmacologically -- |
| Col. 24, line 48 | Delete " pharmaceutically " and substitute -- pharmacologically -- |
| Col. 24, line 64 | Delete " pharmaceutically " and substitute -- pharmacologically -- |
| Col. 25, line 13 | Delete " pharmaceutically " and substitute -- pharmacologically -- |

UNITED STATES PATENT AND TRADEMARK OFFICE
CERTIFICATE OF CORRECTION

PATENT NO. : 4,870,085

DATED : September 26, 1989

INVENTOR(S) : Glaser et al.

It is certified that error appears in the above-identified patent and that said Letters Patent is hereby corrected as shown below:

| | |
|---|---|
| Col. 25, line 28 | Delete " pharmaceutically " and substitute -- pharmacologically -- |
| Col. 26, line 11 | Delete " pharmaceutically " and substitute -- pharmacologically -- |
| Col. 26, line 14 | Delete " pharmaceutically " and substitute -- pharmacologically -- |
| Col. 26, line 22 | Delete " pharmaceutically " and substitute -- pharmacologically -- |
| Col. 26, line 30 | Delete " pharmaceutically " and substitute -- pharmacologically -- |
| Title Page | ABSTRACT: Line 4 delete " or " and substitute -- of -- |

Signed and Sealed this

Twenty-seventh Day of November, 1990

Attest:

HARRY F. MANBECK, JR.

*Attesting Officer*     *Commissioner of Patents and Trademarks*